US00PP16099P2

(12) United States Plant Patent
Hempel

(10) Patent No.: US PP16,099 P2
(45) Date of Patent: Nov. 8, 2005

(54) ***HYDRANGEA* PLANT NAMED 'BELA'**

(50) Latin Name: *Hydrangea paniculata*
Varietal Denomination: Bela

(75) Inventor: Peter Hempel, Billerbeck (DE)

(73) Assignee: HBA, Aalsmeer (NL)

( * ) Notice: Subject to any disclaimer, the term of this patent is extended or adjusted under 35 U.S.C. 154(b) by 22 days.

(21) Appl. No.: 10/924,022

(22) Filed: Aug. 23, 2004

(51) Int. Cl.[7] ..... A01H 5/00
(52) U.S. Cl. ..... Plt./250
(58) Field of Search ..... Plt./250

(56) References Cited

PUBLICATIONS

UPOV 'hit' on 'Bela', UPOV–Rom, GTI Jpuve Retrieval Software, Plant Variety Databases, 2004/06.*

* cited by examiner

*Primary Examiner*—Anne Marie Grunberg
(74) *Attorney, Agent, or Firm*—C. A. Whealy

(57) ABSTRACT

A new and distinct cultivar of *Hydrangea* plant named 'Bela', characterized by its upright and mounded plant habit; strong stems; large durable leaves; dome-shaped inflorescences; and inflorescences with blue-colored flowers.

1 Drawing Sheet

Botanical classification/cultivar designation: *Hydrangea paniculata* cultivar Bela.

BACKGROUND OF THE INVENTION

The present Invention relates to a new and distinct cultivar of *Hydrangea* plant, botanically known as *Hydrangea paniculata*, and hereinafter referred to by the cultivar name Bela.

The new *Hydrangea* is a product of a planned breeding program conducted by the Inventor in Bilderbeck, Germany. The objective of the breeding program was to create new stonger-growing *Hydrangeas* with attractive flower bract coloration and no vernalization requirement.

The new *Hydrangea* originated from a cross-pollination on Jul. 18, 1991 of a proprietary selection of *Hydrangea paniculata* identified as code number 91015, not patented, as the female, or seed, parent with a proprietary selection of *Hydrangea paniculata* identified as code number 91125-13, not patented, as the male, or pollen, parent. The cultivar Bela was discovered and selected by the Inventor as a single plant within the progeny of the stated cross-pollination in a controlled environment in Bilderbeck, Germany on Jul. 29, 1993.

Asexual reproduction of the new cultivar by vegetative cuttings at Bilderbeck, Germany, since Aug. 1, 1993, has shown that the unique features of this new *Hydrangea* are stable and reproduced true to type in successive generations.

SUMMARY OF THE INVENTION

Plants of the cultivar Bela have not been observed under all possible environmental conditions. The phenotype may vary somewhat with variations in environment such as temperature and light intensity without, however, any variance in genotype.

The following traits have been repeatedly observed and are determined to be the unique characteristics of 'Bela'. These characteristics in combination distinguish 'Bela' as a new and distinct cultivar:

1. Upright and mounded plant habit.
2. Strong stems.
3. Large durable leaves.
4. Dome-shaped inflorescences.
5. Inflorescences with blue-colored flowers.

Plants of the new *Hydrangea* differ from plants of female parent selection in the following characteristics:

1. Plants of the new *Hydrangea* have thicker lateral branches than plants of the female parent selection.
2. Plants of the new *Hydrangea* have darker blue-colored flowers than plants of the female parent selection.

Plants of the new *Hydrangea* differ from plants of male parent selection in the following characteristics:

1. Plants of the new *Hydrangea* are larger and stronger than plants of the male parent selection.
2. Plants of the new *Hydrangea* have darker blue-colored flowers than plants of the male parent selection.

Plants of the new *Hydrangea* can be compared to plants of the cultivar Renate Steiniger, not patented. In side-by-side comparisons conducted in Bilderbeck, Germany, plants of the new *Hydrangea* differed from plants of the cultivar Renate Steiniger in the following characteristics:

1. Plants of the new *Hydrangea* had stronger lateral branches than plants of the cultivar Renate Steiniger.
2. Plants of the new *Hydrangea* and the cultivar Renate Steiniger differed in leaf shape.
3. Plants of the new *Hydrangea* had darker blue-colored flowers than plants of the cultivar Renate Steiniger.

Plants of the new *Hydrangea* can be compared to plants of the cultivar Blauer Zwerg, not patented. In side-by-side comparisons conducted in Bilderbeck, Germany, plants of the new *Hydrangea* differed from plants of the cultivar Blauer Zwerg in the following characteristics:

1. Plants of the new *Hydrangea* were larger, more vigorous and stronger than plants of the cultivar Blauer Zwerg.
2. Plants of the new *Hydrangea* had thicker lateral branches than plants of the cultivar Blauer Zwerg.

3. Plants of the new *Hydrangea* and the cultivar Blauer Zwerg differed in leaf shape.
4. Plants of the new *Hydrangea* had darker blue-colored flowers than plants of the cultivar Blauer Zwerg.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Hydrangea*. The photograph comprises a side perspective view of a typical plant of 'Bela' grown in a container.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown in Bilderbeck, Germany, in 15-cm containers in a glass-covered greenhouse and under conditions which closely approximate commercial production conditions. During the production of the plants, day temperatures ranged from 18 to 30° C., night temperatures averaged 15° C. and light levels averaged 35 kilolux. Plants were about one year old when the photograph and description were taken and the pH level of the soil was about 4.4. The photograph and description were taken during the summer.

Botanical classification: *Hydrangea paniculata* cultivar Bela.

Parentage:

*Male, or pollen, parent.*—Proprietary *Hydrangea paniculata* selection identified as code number 91015, not patented.

*Female, or seed, parent.*—Proprietary *Hydrangea paniculata* selection identified as code number 91125-13, not patented.

Propagation:

*Type cutting.*—By vegetative cuttings.

*Time to initiate roots, summer.*—About 14 days at 23° C.

*Time to initiate roots, winter.*—About 18 days at 18° C.

*Time to produce a rooted cutting or liner, summer.*—About four weeks at 23° C.

*Time to produce a rooted cutting or liner, winter.*—About five weeks at 18° C.

*Root description.*—Thick; white to brown in color.

*Rooting habit.*—Freely branching; dense.

Plant description:

*Form/growth habit.*—Upright and mounded plant habit. Strong lateral branches; vigorous growth habit.

*Plant height, soil level to top of plant plane.*—About 45 cm.

*Plant diameter or area of spread.*—About 45 cm.

*Branching habit.*—When pinched, freely branching with about six to nine lateral branches per plant.

*Lateral branches.*—Length: About 20 to 30 cm. Diameter: About 1 cm. Internode length: About 5 cm. Texture: Glabrous. Strength: Strong. Color: Close to 146A.

*Foliage description.*—Leaves large, simple, opposite and durable. Length: About 15 cm. Width: About 15 cm. Shape: Elliptic to obovate. Apex: Acute. Base: Obtuse. Margin: Dentate to serrate. Texture, upper and lower surfaces: Glabrous; smooth to rugose. Venation pattern: Pinnate. Color: Developing and fully expanded foliage, upper surface: Close to 147A. Developing and fully expanded foliage, lower surface: Close to 147B. Venation, upper and lower surfaces: Close to 146A. Petiole: Length: About 3 cm. Diameter: About 5 mm. Texture, upper and lower surfaces: Smooth, glabrous. Color, upper and lower surfaces: Close to 146A.

Flower description:

*Flower type and habit.*—Single flowers arranged on terminal panicles; panicles large and semi-hemispherical or dome-shaped. Flowers persistent. Flowers not fragrant.

*Natural flowering season.*—Intermittent flowering during the summer in The Netherlands.

*Flower longevity.*—Flowers last about four months on the plant.

*Quantity of flowers.*—Freely flowering; about 40 to 50 per panicle.

*Panicle diameter.*—About 35 cm.

*Panicle height.*—About 10 cm.

*Flower diameter.*—About 5 cm.

*Flower depth (height).*—About 5 mm.

*Flower buds.*—Length: About 5 mm. Diameter: About 3 mm. Shape: Ovoid. Color: 104D.

*Petals.*—Arrangement: Five in a single whorl. Length: About 4 mm. Width: About 2 mm. Shape: Ovate. Apex: Acute. Base: Attenuate. Margin: Entire. Texture, upper and lower surfaces: Smooth, glabrous. Color: When opening, upper and lower surfaces: Close to 113A; towards the base, 113D; color becoming closer to 148A with development. Fully opened, upper and lower surfaces: Close to 113A; towards the base, 113D.

*Sepals.*—Quantity per flower: Four, fused into a calyx. Length: About 2.5 cm. Width: About 2.5 cm. Shape: Ovate to deltoid. Apex: Acute. Base: Obtuse. Margin: Entire. Texture, upper and lower surfaces: Smooth, glabrous. Color: When opening and fully opened, upper and lower surfaces: Towards the apex, 98A; towards the base, 117B; color becoming closer to 79A with development.

*Pedicels.*—Angle: About 45° from vertical. Strength: Strong. Length: About 3 cm. Diameter: About 1.5 mm. Color: 98A and 117B.

*Reproductive organs.*—Stamens: Quantity per flower: About three. Anther shape: Conical. Anther length: About 1 mm. Anther color: 98C. Pollen amount: Abundant. Pollen color: Close to 155D. Pistils: Pistil quantity per flower: About eight. Pistil length: About 4 to 5 mm. Stigma shape: Oval. Stigma color: Close to 155D. Style length: About 2 to 3 mm. Style color: 108D. Ovary color: 142B. Seed: Length: About 1 mm. Diameter: About 0.2 mm. Color: Brownish.

Disease/pest resistance: Under commercial production conditions, plants of the new *Hydrangea* have not been observed to be resistant to pathogens or pests common to *Hydrangea*.

Temperature tolerance: Plants of the new *Hydrangea* have been shown to be tolerant to temperatures ranging from about 3 to about 40° C.

It is claimed:

1. A new and distinct cultivar of *Hydrangea* plant named 'Bela', as illustrated and described.

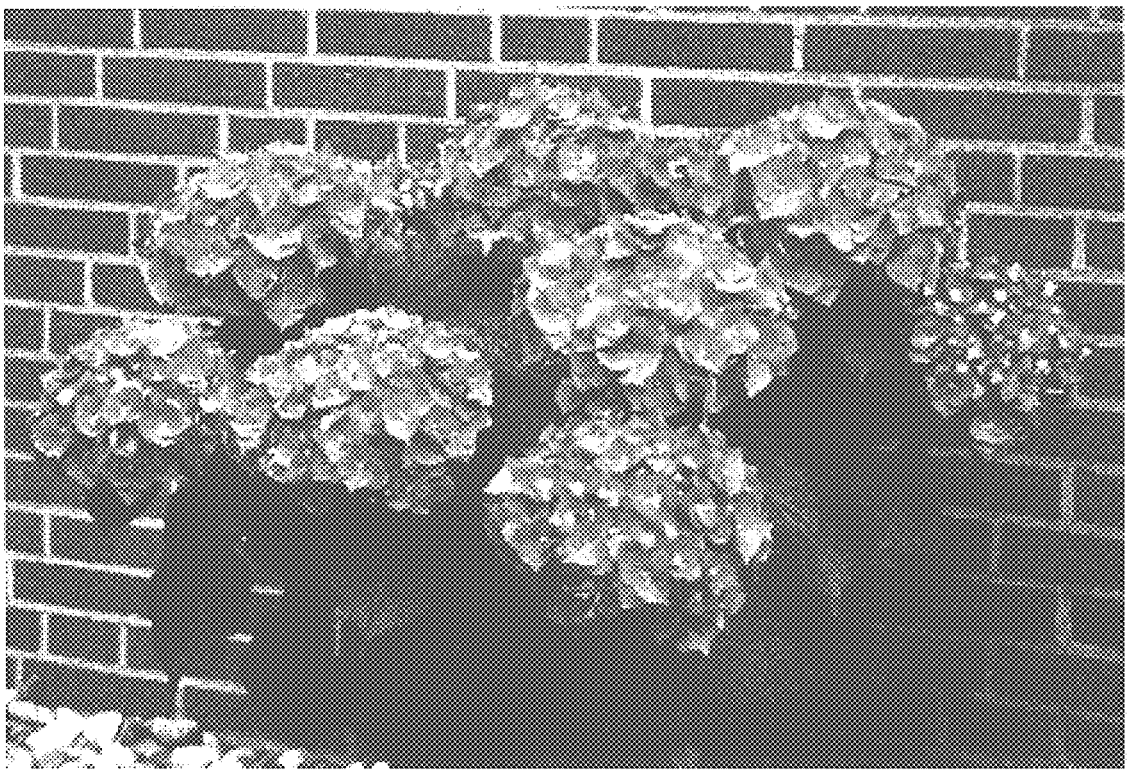

* * * * *